(12) United States Patent
Rezvani

(10) Patent No.: US 6,429,660 B1
(45) Date of Patent: Aug. 6, 2002

(54) PROCESS FOR MINIMIZING CROSS-TALK IN DIAGNOSTIC SIGNALS OF A PH SENSOR

(75) Inventor: Behzad Rezvani, Anaheim, CA (US)

(73) Assignee: Rosemount Analytical Inc., Irvine, CA (US)

( * ) Notice: Subject to any disclaimer, the term of this patent is extended or adjusted under 35 U.S.C. 154(b) by 21 days.

(21) Appl. No.: 09/748,881

(22) Filed: Dec. 27, 2000

(51) Int. Cl.[7] ............................................. G01N 27/416
(52) U.S. Cl. ........................................ 324/426; 324/425
(58) Field of Search ................................. 324/426, 425, 324/438, 444; 204/406, 407, 411, 412

(56) References Cited

U.S. PATENT DOCUMENTS

| | | | |
|---|---|---|---|
| 5,334,940 A | 8/1994 | Blades | 324/442 |
| 5,469,070 A | 11/1995 | Koluvek | 324/713 |
| 5,621,669 A | 4/1997 | Bjornsson | 364/571.01 |
| 5,970,428 A * | 10/1999 | Brennan | 324/425 |

* cited by examiner

Primary Examiner—Edward H. Tso
Assistant Examiner—Lawrence Luk
(74) Attorney, Agent, or Firm—Westman, Champlin & Kelly, P.A.

(57) ABSTRACT

A pH analyzer is operated to measure pH of a solution by applying a reference electrode current, $I_{REF}$, to a reference electrode of a pH sensor and an ion-specific electrode current, $I_{GLASS}$, to an ion-specific electrode of the pH sensor. The currents to the reference electrode and ion-specific electrode are multiplexed to avoid cross-talk. Multiplexing the currents provides a more accurate measurement of electrode impedance for diagnostic purpose. A current spike is optionally added to the reference electrode current to discharge any charge in the solution due to the reference electrode current.

20 Claims, 1 Drawing Sheet

PROCESS FOR MINIMIZING CROSS-TALK IN DIAGNOSTIC SIGNALS OF A PH SENSOR

FIELD OF THE INVENTION

This invention relates to pH sensors for measuring pH of a solution, and particularly to minimizing cross-talk between currents carried by electrodes of a pH sensor.

BACKGROUND OF THE INVENTION

Sensors that measure ion content, also known as pH sensors, are used in industrial process control systems to measure the hydrogen ($H^+$) or hydroxyl ($OH^-$) ion content, or pH, of a solution of the industrial process. pH sensors employ at least two electrodes, an ion-specific electrode (commonly called a glass electrode due to its construction) and a reference electrode. A pH analyzer operates the pH sensor by measuring a voltage across both the ion-specific electrode ($I_{GLASS}$) and the reference electrode ($I_{REF}$). Thus, the voltage between a common potential, such as electrical ground, and each of the ion-specific electrode ($V_{GLASS}$) and the reference electrode ($V_{REF}$) is measured, and the difference between the two voltages ($V_{GLASS}-V_{REF}$) represents the pH value. The sensor is calibrated so that there is a known relationship between $V_{GLASS}$ and $V_{REF}$ when the sensor is in a neutral (pH=7.0) solution.

The impedances of the ion-specific and reference electrodes are used for diagnostic and maintenance purposes. Thus, if a sensor becomes cracked or otherwise deteriorates, the ability of the sensor to accurately measure the ion content of the solution also deteriorates. Electrode deterioration is determined from the impedance (resistance) of the electrodes. If the impedance of one electrode changes, the sensor may require re-calibration or replacement.

The impedance of the ion-specific electrode may be significantly greater than that of the reference electrode; the ion-specific electrode often exhibiting as much as 10,000 times the impedance of the reference electrode. Consequently, the current to the reference electrode may be significantly greater than that to the ion-specific electrode; $I_{REF}$ often being as much as 10,000 times $I_{GLASS}$. With both $I_{GLASS}$ and $I_{REF}$ flowing through the solution at the same time, cross-talk between the currents in the ion-specific and reference electrodes may alter the current flows in the solution, and hence the voltage outputs, resulting in error in impedance measurements of the electrodes. The present invention is directed to a method of multiplexing $I_{GLASS}$ and $I_{REF}$ to minimize cross-talk to improve impedance measurements of the electrodes.

SUMMARY OF THE INVENTION

According to the present invention, cross-talk between the reference and ion-specific electrodes is minimized by applying the first current, $I_{GLASS}$, to the ion-specific electrode during a first time period and applying the second current, $I_{REF}$, to the reference electrode a second time period.

In a preferred form of the invention, the first and second currents are substantially direct (DC) currents and application of the first and second currents to their respective electrodes is interleaved so that the first current is applied to the ion-specific electrode while the second current is off and the second current is applied to the reference electrode while the first current is off.

In another preferred form of the invention, a current spike is added to the second current whenever the second current changes to off. The current spike has a value to discharge any charge in the solution due to the second current.

In another preferred form of the invention, the ion-specific electrode and the reference electrode, together with a common electrode, are applied to a solution. A difference between voltages at the ion-specific electrode, $V_{GLASS}$, and the reference electrode, $V_{REF}$, each relative to the common electrode, is a measure of pH of the solution.

In another preferred form of the invention, the impedance of the ion-specific electrode is calculated based on the first current, $I_{GLASS}$, and the voltage measured between the ion-specific electrode and the common electrode.

DETAILED DESCRIPTION OF THE PREFERRED EMBODIMENTS

Figure 1:
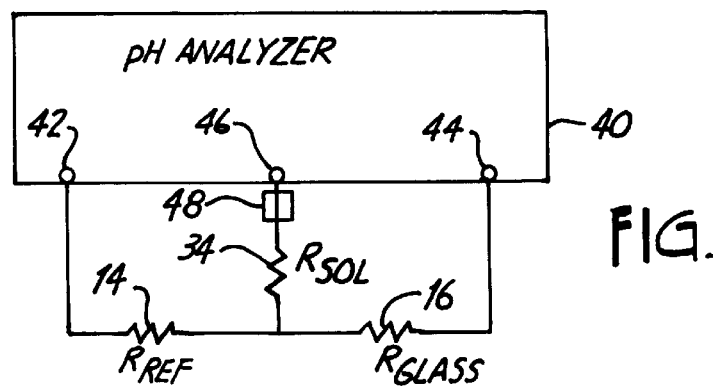
FIG. 1 is a schematic diagram illustrating the resistance circuit of a pH sensor in a sample solution, as coupled to a pH analyzer.

FIG. 1 is a circuit diagram illustrating the equivalent circuit of a pH sensor 10 having a reference electrode 14 and an ion-specific electrode 16 connected to terminals 42 and 44, respectively, of a pH analyzer 40. Electrodes 14 and 16 are exposed to a sample solution 34. Analyzer 40 includes a third terminal 46 coupled to a common electrical potential, such as electrical ground. Terminal 46 is coupled to an electrode 48 which is also exposed to sample solution 34.

The operation of analyzer 40 to measure pH of solution 34 is described in U.S. Pat. No. 5,469,070 granted Nov. 21, 1995 to Roland H. Koluvek for "Circuit for Measuring Source Resistance of a Sensor". Substantially direct current signals (DC), in the form of successive positive and negative current pulses, are applied to both the reference electrode input terminal 42 and the ion-specific electrode input terminal 44. The average voltage (between peaks) across terminals 42 and 46 ($V_{REF}$) is measured, representing the voltage across reference electrode 14 and the sample solution 34. For example, if the DC voltage, $V_{REF}$, across terminals 42 and 46 alternates between +100 millivolts and −80 millivolts, the average voltage is +10 millivolts. Similarly, the average voltage across terminals 44 and 46 ($V_{GLASS}$) is measured, representing the voltage across ion-specific electrode 16 and solution 34. The difference between the two voltage measurements is a measure of pH.

Analyzer 40 is calibrated by measuring the impedance of the reference electrode and ion-specific electrode of the sensor using the reference electrode current, $I_{REF}$, and the ion-specific electrode current, $I_{GLASS}$. The analyzer is adjusted (calibrated) so that the relationships of voltage, $V_{REF}$, between terminals 42 and 46, and the voltage, $V_{GLASS}$, between terminals 44 and 46, is known when the solution is neutral (pH 7.0). A change in the relationship of the voltages is representative of the pH of the solution.

It is common for analyzer 40 to perform diagnostic tests on the sensor while measuring pH of the solution. Diagnostic tests are typically performed by measuring the impedance (resistance) values of the ion-specific and reference electrodes to identify any deterioration of the sensor. The resistance measurement is performed simply by dividing the peak voltages between the respective terminals 42 and 46, and 44 and 46. For example, if the voltage, $V_{REF}$, across terminals 42 and 46 alternates between +100 millivolts and −80 millivolts, the peak swing voltage is 180 millivolts, which is divided by the reference current, $I_{REF}$, to calculate $R_{REF}$. The resistance of the ion-specific electrode, $R_{GLASS}$, might be significantly greater than that of the reference electrode, $R_{REF}$; a ratio of 10,000 to 1 being common. Consequently, the current applied to the reference electrode terminal 42 ($I_{REF}$) might be similarly large compared to the current applied to the ion-specific electrode terminal 44 ($I_{GLASS}$); it being common that $I_{REF}$ be 10,000 times $I_{GLASS}$. When the sample solution exhibits a high impedance the high current difference between $I_{REF}$ and $I_{GLASS}$ creates cross-talk at the electrodes, which is reflected as noise in the output voltages $V_{REF}$ and $V_{GLASS}$. This noise can lead to error in the measurement of the impedance of the ion-specific electrode, and hence error in the calibration of the apparatus and error in diagnostics. The present invention minimizes cross-talk by multiplexing the two currents $I_{REF}$ and $I_{GLASS}$.

Cross-talk and noise usually do not significantly affect measurement of the impedance of the reference electrode, $R_{REF}$, because the current through the reference electrode, $I_{REF}$, is usually so high in relation to the current through the ion-specific electrode, $I_{GLASS}$, that small changes in the voltage across reference electrode 14 due to cross-talk do not materially affect computation of $R_{REF}$. The current, $I_{GLASS}$, through the ion-specific electrode, however, is small such that even small changes in the voltage across ion-specific electrode 16 affects computation of $R_{GLASS}$. Accordingly, cross-talk and noise may adversely affect the accuracy of the computation of $R_{GLASS}$. While the invention is described herein to overcome problems of cross-talk and noise in the computation of $R_{GLASS}$, the invention is useful with to overcome cross-talk and noise problems affecting the computation of $R_{REF}$, such as for sensors whose reference electrode impedance is sufficiently close to the ion-specific electrode impedance that cross-talk and noise might affect the accuracy of measurement of $R_{REF}$.

Figure 2:
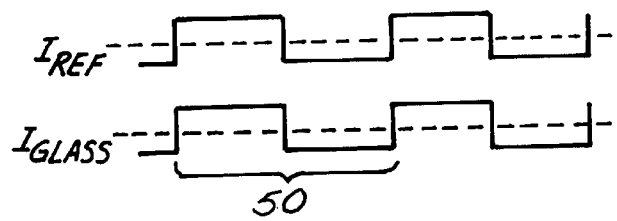
FIG. 2 is a timing diagram of current to the electrodes of a pH sensor in accordance with the prior art.

FIG. 2 illustrates the timing of the $I_{REF}$ and $I_{GLASS}$ currents as described in the aforementioned Koluvek patent. As shown in FIG. 2, the $I_{REF}$ and $I_{GLASS}$ currents are substantially DC currents in a first (positive) direction to the respective electrodes to cause the voltage at terminals 42 and 44 to go high (positive) during a first portion of a cycle 50, and the currents are in the opposite (negative) direction to cause the voltages at terminals 42 and 44 to go low (negative) during a second portion of cycle 50. The magnitude of $I_{REF}$ may be as much as 10,000 times, or more, than $I_{GLASS}$. Consequently, the solution, $R_{SOL}$, carries the sum of $I_{REF}+I_{GLASS}$, creating cross-talk in the voltages between the two electrodes. This cross-talk affects the accurate calculation of the sensor and measurement of the ion-specific electrode impedance, $R_{GLASS}$, thereby affecting maintenance and diagnostic procedures.

Figure 3:
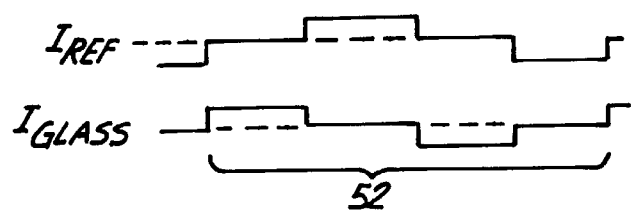
FIGS. 3–5 are timing diagrams of current to the electrodes of a pH sensor in accordance with different embodiments of the present invention.

To overcome the problem of cross-talk, the present invention multiplexes the $I_{REF}$ and $I_{GLASS}$ currents so that when one of the substantially DC currents flows (in either direction) the other does not flow. Consequently, when one of $I_{GLASS}$ and $I_{REF}$ is on or flowing (in either direction), the other is terminated or off. Thus, as shown in FIG. 3, the $I_{REF}$ and $I_{GLASS}$ currents assume three DC states (positive, negative and off) during four periods of a cycle 52. The $I_{REF}$ and $I_{GLASS}$ currents are multiplexed so that the $I_{REF}$ and $I_{GLASS}$ current states are arranged positive, off, negative, off, positive, etc., so that when one current is positive or negative, the other is off. Thus, the currents are interleaved so that during a first period of cycle 52, $I_{REF}$ is off and $I_{GLASS}$ flows in a positive direction. During the second period of cycle 52, $I_{REF}$ is positive and $I_{GLASS}$ is off. During the third period, $I_{REF}$ is off and $I_{GLASS}$ is negative. During the fourth period, $I_{REF}$ is negative and $I_{GLASS}$ is off. Consequently, current through the sample solution is only either the ion-specific electrode current $I_{GLASS}$ or the reference electrode current $I_{REF}$. Consequently, cross-talk is minimized, resulting in greater accuracy of the voltage measurements and greater accuracy of the impedance calculations, particularly for the ion-specific electrode. As a result, the operation of the industrial process control system can be more accurately diagnosed, leading to better maintenance of the system.

The aforementioned Koluvek patent describes measurement of voltages $V_{REF}$ and $V_{GLASS}$ during periods while both are positive and both are negative. The average of the high and low $V_{REF}$ voltages and the average of the high and low $V_{GLASS}$ voltages are compared to determine pH measurement. The present invention similarly measures the high and low $V_{REF}$ and $V_{GLASS}$ voltages and uses the average to determine pH. However, instead of measuring the high $V_{REF}$ and $V_{GLASS}$ voltages during a first period of cycle 50 shown in FIG. 2 and the low $V_{REF}$ and $V_{GLASS}$ voltages during a second period of cycle 50, the present invention measures the high and low $V_{REF}$ and $V_{GLASS}$ voltages during mutually exclusive periods. More particularly, in FIG. 3, the voltage $V_{REF}$ between terminals 42 and 46 is measured during the second and fourth periods of cycle 52 and the voltage $V_{GLASS}$ between terminals 44 and 46 is measured during the first and third periods of cycle 52.

Figure 4:
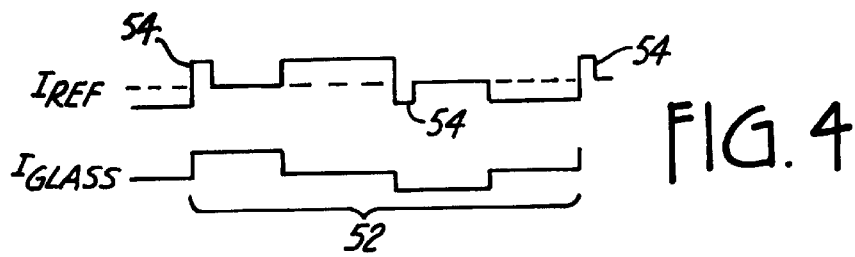

FIG. 4 illustrates a modification of the multiplexing scheme illustrated in FIG. 3 in which a current pulse or spike 54 is added to the $I_{REF}$ current at the beginning of each period during which the reference current is terminated or off (when $V_{REF}$ is otherwise neutral). Current pulse is of opposite direction to the direction of the $I_{REF}$ current immediately prior to the current pulse. Thus, current pulse 54 is positive following a period of negative $I_{REF}$ and current pulse 54 is negative following a period of positive $I_{REF}$. The current pulses serve to discharge polarization of the electrode that might be established when the prior positive or negative reference current was applied to the reference current.

More particularly, the ions in the sample solution may establish a capacitance between the reference electrode 14 and the ion-specific electrode 16. When a high $I_{REF}$ current ($I_{REF}$ positive or negative) is applied to reference electrode 14 the capacitance of sample solution 34 is charged. The ion-specific electrode voltage $V_{GLASS}$ is affected by any charge on the electrode that is carried over to the period when the reference current is neutral and the ion-specific electrode current $I_{GLASS}$ is positive or negative. Therefore, current pulse 54 is applied to the reference electrode to discharge polarization on the electrode. The size and duration of current pulse 54 will depend on the expected charge on the solution, which will vary depending on the solution composition and its pH range. pH analyzer 40 may include a microprocessor programmed to select the size and duration of pulse 54 based on operator input of the solution composition and the measured pH.

In most cases, it is not necessary to include a charge dissipating current pulse 54 in the ion-specific electrode current $I_{GLASS}$ because the magnitude of the reference electrode current $I_{REF}$ is so much higher ion-specific electrode current $I_{GLASS}$ that any charge due to $I_{GLASS}$ has little or no effect on voltage measurement. However, a charge-dissipating current pulse might be included in the ion-specific electrode current where the magnitudes of the $I_{REF}$ and $I_{GLASS}$ currents are closer such that the ion-specific electrode might become polarized.

Figure 5:
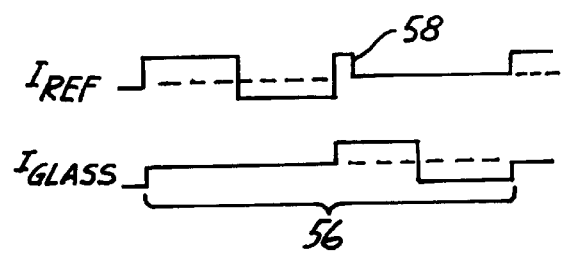

FIG. 5 illustrates another embodiment of the multiplexing of $I_{REF}$ and $I_{GLASS}$ in which each current is reversed during successive periods of cycle 56, and then off or terminated during the remaining two periods. Consequently, $I_{REF}$ and $I_{GLASS}$ are interleaved by applying successive positive and negative $I_{REF}$ followed by successive positive and negative $I_{GLASS}$, etc. As in the case of the embodiments of FIGS. 3 and 4, $I_{GLASS}$ is positive or negative only when $I_{REF}$ is off and $I_{REF}$ is positive or negative only when $I_{GLASS}$ is off. Thus, $I_{REF}$ is positive and $I_{GLASS}$ is off so that $V_{REF}$ is high and $V_{GLASS}$ is neutral during the first period of cycle 56, $I_{REF}$ is negative and $I_{GLASS}$ remains off so that $V_{REF}$ is low and $V_{GLASS}$ remains neutral during the second period, $I_{REF}$ is off and $I_{GLASS}$ is positive so that $V_{REF}$ is neutral and $V_{GLASS}$ is high during the third period, and $I_{REF}$ remains off and $I_{GLASS}$ is negative so that $V_{REF}$ remains neutral and $V_{GLASS}$ is low during the fourth period. Consequently, current through the sample solution is only either the ion-specific electrode current $I_{GLASS}$ or the reference electrode current $I_{REF}$, and cross-talk is minimized resulting in greater accuracy of the impedance measurements.

If desired, the reference electrode current $I_{REF}$ may include a current pulse or spike 58 to discharge any capacitance in solution 34 as described in connection with FIG. 4. In this case, however, since the second period of the reference electrode current is opposite the first period, no pulse or spike 58 is necessary. Instead, the pulse or spike 58 is used only when the reference electrode current $I_{REF}$ is changed from either positive or negative to neutral (thereby avoiding any residual charge when the ion-specific electrode current $I_{GLASS}$ is applied to ion-specific electrode 16).

While the pH sensor has been characterized as containing a reference electrode and an ion-specific electrode, the ion-specific electrode is not necessarily constructed of glass, and may be any suitable material. Hence, the term "glass" is not limiting on the construction of the ion-specific electrode. Moreover, while the present invention has been described in connection with multiplexing currents to the reference and ion-specific electrodes of a pH sensor, the multiplexing is applicable to industrial process control sensors employing currents to a reference electrode and a sensing electrode.

Although the present invention has been described with reference to preferred embodiments, workers skilled in the art will recognize that changes may be made in form and detail without departing from the spirit and scope of the invention.

What is claimed is:

1. A process of operating a pH analyzer to measure pH of a solution, comprising steps of:
   a) providing a pH sensor having an ion-specific electrode and a reference electrode, the ion-specific electrode being in contact with the solution and designed to provide an electrical potential based on the pH of the solution, the reference electrode being designed to provide a reference electrical potential and being coupled to the ion-specific electrode through the solution;
   b) applying the pH sensor and a common electrode to the solution;
   c) measuring the pH of the solution during a first cycle of operation by
      c1) applying a first current, $I_{GLASS}$, to the ion-specific electrode during a first time period,
      c2) applying a second current, $I_{REF}$, to the reference electrode during a second time period that is mutually exclusive of the first time period,
      c3) measuring a voltage, $V_{GLASS}$, between the ion-specific electrode and the common electrode,
      c4) measuring a voltage, $V_{REF}$, between the reference electrode and the common electrode,
      c5) identifying the pH of the solution based on a difference between the measured voltages $V_{GLASS}$ and $V_{REF}$.

2. The process of claim 1, wherein the first and second currents are substantially direct currents.

3. The process of claim 2, wherein the first and second currents alternate between positive and negative directions, wherein steps (c1) and (c2) are performed by interleaving application of the first and second currents to their respective electrodes so that the positive direction of the first and second current occurs during mutually exclusive time periods and the negative direction of the first and second currents occurs during mutually exclusive time periods.

4. The process of claim 2, wherein the first and second currents alternate between a first state wherein the respective current is off and a second state wherein the respective current alternates between first and second flow directions, wherein steps (c1) and (c2) are performed by interleaving application of the first and second currents to their respective electrodes so that the first current alternates between its first and second directions while the second current is off and the second current alternates between its first and second directions while the first current is off.

5. The process of claim 4, further comprising the step of applying a current spike to the second current whenever the value of the second current changes from flowing to off.

6. The process of claim 2, wherein the first and second currents alternate between off and flowing in first and second directions, wherein steps (c1) and (c2) are performed by interleaving application of the first and second currents to their respective electrodes so that the first and second currents flow in the first direction during contiguous time periods and the first and second currents flow in the second direction during contiguous time periods, and the first current is off during time periods that the second current flows and the second current is off during time periods that the first current flows.

7. The process of claim 6, further comprising the step of applying a current spike to the second current whenever the value of the second current changes from flowing to off.

8. The process of claim 2, wherein the first and second currents alternate between flowing in first and second directions and off, wherein steps (c1) and (c2) are performed by interleaving application of the first and second currents to their respective electrodes so that the first current is applied to the ion-specific electrode in first and second current directions while the second current is off and the second current is applied to the reference electrode in first and second directions while the first current is off.

9. The process of claim 8, further comprising the step of applying a current spike to the second current whenever the value of the second current changes from flowing to off.

10. The process of claim 1, further comprising the step of calculating an impedance of the ion-specific electrode based on the first current and the voltage measured in step (c3).

11. A process of minimizing cross-talk between a sensing electrode and a reference electrode of a sensor during a measurement of a process variable, the sensing electrode being in association with the process variable and designed to provide an electrical potential based on the process variable and the reference electrode being designed to provide a reference electrical potential and being coupled to the sensing electrode through the process variable, the sensor further having a common electrode in association with the process variable, the process comprising steps of a) applying a first current, $I_{GLASS}$, to the sensing electrode during a first time period;

b) applying a second current, $I_{REF}$, to the reference electrode during a second time period, the first and second time periods being mutually exclusive, c) measuring a voltage, $V_{GLASS}$, between the sensing electrode and the common electrode, d) measuring a voltage, $V_{REF}$, between the reference electrode and the common electrode, and e) identifying the measurement of the process variable from the measured voltages.

12. The process of claim 11, wherein the first and second currents are substantially direct currents.

13. The process of claim 12, wherein the first and second currents alternate between positive and negative directions, wherein steps (a) and (b) are performed by interleaving application of the first and second currents to their respective electrodes so that the positive direction of the first and second current occurs during mutually exclusive time periods and the negative direction of the first and second currents occurs during mutually exclusive time periods.

14. The process of claim 12, wherein the first and second currents alternate between a first state wherein the respective current is off and a second state wherein the respective current alternates between first and second flow directions, wherein steps (a) and (b) are performed by interleaving application of the first and second currents to their respective electrodes so that the first current alternates between its first and second directions while the second current is off and the second current alternates between its first and second directions while the first current is off.

15. The process of claim 12, wherein the first and second currents alternate between off and flowing in first and second directions, wherein steps (a) and (b) are performed by interleaving application of the first and second currents to their respective electrodes so that the first and second currents flow in the first direction during contiguous time periods and the first and second currents flow in the second direction during contiguous time periods, and the first current is off during time periods that the second current flows and the second current is off during time periods that the first current flows.

16. The process of claim 15, further comprising the step of applying a current spike to at least one of the first and second currents whenever the one current changes from flowing to off.

17. The process of claim 16, wherein the current spike has a direction opposite the direction of the one current immediately prior to the change to off.

18. The process of claim 12, wherein the first and second currents alternate between flowing in first and second directions and off, wherein steps (a) and (b) are performed by interleaving application of the first and second currents to their respective electrodes so that the first current is applied to the sensing electrode in first and second current directions while the second current is off and the second current is applied to the reference electrode in first and second directions while the first current is off.

19. The process of claim 11, wherein the process variable is a pH of a solution.

20. The process of claim 11, further comprising the step of calculating an impedance of the sensing electrode based on the first current and the voltage measured in step (c).

* * * * *